(12) United States Patent
Salinas et al.

(10) Patent No.: US 6,511,456 B1
(45) Date of Patent: Jan. 28, 2003

(54) SAFETY LINE SYSTEM

(76) Inventors: Terri L. Salinas, 131 Tyrone Ct., Vacaville, CA (US) 95688; Gail Barton-Hay, 16280 Blackie Rd., Salinas, CA (US) 93907

( * ) Notice: Subject to any disclaimer, the term of this patent is extended or adjusted under 35 U.S.C. 154(b) by 106 days.

(21) Appl. No.: 09/639,057

(22) Filed: Aug. 15, 2000

(51) Int. Cl.$^7$ .......................... A61M 11/00; A61M 5/14
(52) U.S. Cl. ...................... 604/93.01; 604/80; 604/173
(58) Field of Search .................. 604/93.01, 80, 604/171, 173, 27, 48, 246, 523, 533

(56) References Cited

U.S. PATENT DOCUMENTS

| | | | | |
|---|---|---|---|---|
| 4,795,429 A | * | 1/1989 | Feldstein | 604/80 |
| 5,224,932 A | * | 7/1993 | Lappas | 604/80 |
| 5,423,750 A | * | 6/1995 | Spiller | 604/80 |

* cited by examiner

*Primary Examiner*—Chen-Wen Jiang
(74) *Attorney, Agent, or Firm*—William S. Bernheim

(57) ABSTRACT

An improved method for simultaneous intravenous delivery of multiple medications by use of prematched tubing between medication source and patient's IV.

1 Claim, No Drawings

SAFETY LINE SYSTEM

BACKGROUND OF THE INVENTION

1. Field of Invention

This invention relates to a method of prematching colors with medications and/or nutrients for delivery to patients by intravenous catheters to provide better monitoring of such delivery.

2. Relevant Prior Art

As part of most intensive medical emergencies and hospitalizations, the patient is set up with an intravenous ("IV") feed line for delivery of fluids, nutrients and/or medications. In the past few years, many new medications have become available and many patients are on multiple medications, nutrients and/or fluids, which during treatments and hospitalizations are induced through a single IV feed line by piggybacking. The feed or main line has "y" injection sites spaced along the main line. IVs are essential when the patient is unconscious or introduction of medication by mouth is inappropriate due to type of medication, time or stomach contents. IVs also have the advantage of better monitoring the amount of medication and the rate of delivery.

There are problems. How does one quickly identify which line contains which medications, nutrients or fluids. There is typically one main line administering water or a saline solution. A bottle or bag containing medication, fluid or nutrient to be delivered can be placed in flow communication with the patient by attaching a line in flow communication between the bag or bottle and a "y" injection site of the main line. The line containing medication, nutrient or fluid typically has a needle at the distal end to be pushed through a diaphragm at the "y" injection site. The main line solution and various medication bottles or bags are hung on an IV pole and are gravity fed or administered by an infusion pump to the patient. One or more slide clamps along the lines control the rate of flow. Time is sometimes critical and the fastest method to stop a single feed is to pull the correct line end from the "y" site or clamp it closed. Unfortunately, if the IV administration lines are tangled and identical, the correct line must be traced forward from the particular bag or bottle to the clamp or to its "y" site. As IV administration lines have multiplied even in what was previously a simple case, one can appreciate the confusion and possibilities for error.

For example, most labor and delivery sections of a hospital use three or four continuous medications. It is not uncommon to induce birth with one medication while additionally medicating with other medications. This is especially true in problem pregnancies and multiple births. At times it is critical to change the rate of flow or disconnect the line from one of several medications. Time may be critical. If all lines are identical, then the line must be traced forward from the medication to the desired clamp or all the way forward to the main line. This delays action and errors may occur due to the wrong line being clamped or disconnected.

The hospital setting provides great opportunities for medication errors. Hospitals are open seven days a week and 24 hours a day. A particular patient may be seen by several doctors and multiple nurses. All these individuals need to understand quickly and accurately what medications are being administered and in what doses the medications are being delivered to a patient. Delivery lines are typically long and draped and can become intertwined.

Two relevant patents are U.S. Pat. No. 5,423,750 to Spiller and U.S. Pat. No. 4,654,026 to Underwood.

SUMMARY OF THE INVENTION

Objects of the Invention

It is an object of this invention to provide a system which speeds identification of a medication for regulation or disconnection.

A further object is to have a system which reduces the chances of error by disconnection or misregulation of medication being delivered to a patient.

DESCRIPTION OF PREFERRED EMBODIMENT

This invention consists of a method for better monitoring of the delivery of simultaneous intravenous medications to a patient. The method includes several steps. Hospitals are typically divided into departments by level of service and type of service. Examples include ICU (Intensive Care Unit), CU (Cardiac Unit), OB-GYN. Each department will have medications that are used which are unique to that specialty.

A department's frequently used intravenous drugs are identified. Each drug is assigned a particular color. Suitable colors include but are not limited to red, white, blue, green, yellow, purple, orange, brown, gray. Medications are assigned a particular color. Standard delivery tubing can be tinted during manufacture to have the assigned color. The medication is matched to its assigned color tubing and hung on a pole. A matching color tag is attached to a reservoir, a bag or bottle, containing the individual medication. This provides another visual clue to prevent errors when a particular bag with medications becomes empty and needs to be replaced and also when the delivery rate needs to be changed or the medication stopped entirely. When needed, the color tagged bag with its color-matched line is hung from the intravenous pole of the patient and matched line.

As an example, for an ICU (Intensive Care Unit) the following tinted tube scheme is suggested:

1. Vasopressors—such as Dopamine, Levophed, and Dobutamine would be delivered through a green-tinted tube. This color is chosen because this class of drugs will raise blood pressure—as in green=go=up
2. Electrolytes—such as Magnesium and Potassium would use an orange tinted tube. This color is chosen because oranges are high in potassium.
3. Anticoagulants—such as Heparin and Aggrestat would use a pink tinted tube. This color is chosen because blood is pink.
4. Vasodilators—such as Nitroglycerine, and Nipride would use a red tinted tube. This color is chosen because they will cause the blood pressure to drop (go down)—red=stop=down.
5. Anti-arrhythmic—such as Lidocaine would use a yellow tube.

As an example, for Labor and Delivery the following tinted tube scheme is suggested:

1. Oxytocin—such as Pitocin would use a red tinted tube. Very dangerous if too much is given. Red=don't touch
2. Magnesium Sulfate—would use a green tinted tube. No reason.

Frequently used medications such as Insulin, antibiotics and narcotics should be assigned a consistent color throughout an institution such as a hospital. The IV bags and or bottles should continue to be clear so that contamination and sediments could be visualized. The contents of the bags or bottles with the medication should be identified with a white label with a color border that corresponds with the color of the tinted tubing. This should also reduce errors when a bag runs out of fluid and a new bag needs to be hung by providing an additional visual clue as to the medication needed. These color-medication combinations are just suggestions. There are many more drugs and many different settings—such as ER, transplant units, cardiac units, dialysis units, ICU for newborns and pediatrics, paramedic units, home health care and skilled nursing facilities.

There could also be different shades of the same color—such as dark green vs light green tint. This would not be done on the same patient.

Drip chambers should remain clear and these color tinted tubings would always be "piggybacked" into the clear, main line in which there is no medication present. The main line would always be clear to provide a visual check for turbidity, precipitate and back flow of blood from the IV site in the patient. Since the rule would be to never inject medication into the tinted tubing there would be no need for more than one "y" injection site. The tinted tubing should have no more than one "y" injection site and it should be located near the distal end, so that if needed, a health professional could aspirate any air that might be in the tubing. The clear tubing could have as many "y" injection sites as the health care facility desired since these sites are where the color tinted tubing with the medication would be "piggybacked".

We claim:

1. A method for improved safety in the simultaneous intravenous delivery of multiple medications through one main delivery line in which individual medications are placed in separate reservoirs which are in turn fed into the main delivery line comprising:

a. identifying more than one frequently used medication in a facility and assigning a unique color to each such medication;

b. when medications are to be fed simultaneously to a patient in the facility with a main delivery line and multiple medications fed to the line, securing for each medication which has been assigned a color, tubing tinted that color and a matching white label bordered with that color;

c. Adding the medication to a reservoir placing the bordered label on the reservoir and using the tinted tubing to connect the reservoir to the main line.

* * * * *